United States Patent
Gotoh

(10) Patent No.: US 10,881,372 B2
(45) Date of Patent: Jan. 5, 2021

(54) X-RAY IMAGING APPARATUS

(71) Applicant: Shimadzu Corporation, Kyoto (JP)

(72) Inventor: Keita Gotoh, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 15 days.

(21) Appl. No.: 16/217,950

(22) Filed: Dec. 12, 2018

(65) Prior Publication Data

US 2020/0187891 A1    Jun. 18, 2020

(51) Int. Cl.
  *A61B 6/00* (2006.01)
  *G06T 1/00* (2006.01)
  *G01R 19/165* (2006.01)

(52) U.S. Cl.
  CPC ............ *A61B 6/54* (2013.01); *A61B 6/52* (2013.01); *A61B 6/56* (2013.01); *G01R 19/16542* (2013.01); *G06T 1/0007* (2013.01); *A61B 6/461* (2013.01); *G06T 2207/10116* (2013.01)

(58) Field of Classification Search
  CPC ............... A61B 6/54; G01R 19/16542
  See application file for complete search history.

(56) References Cited

U.S. PATENT DOCUMENTS

| | | | |
|---|---|---|---|
| 2015/0071414 A1* | 3/2015 | Oda | A61B 6/4283 378/207 |
| 2016/0074000 A1* | 3/2016 | Uehara | A61B 6/547 378/69 |

FOREIGN PATENT DOCUMENTS

| | | |
|---|---|---|
| JP | 2005-027739 A | 2/2005 |
| JP | 2008-073121 A | 4/2008 |
| JP | 2010-094327 A | 4/2010 |
| JP | 2011-019661 A | 2/2011 |
| JP | 2011-035791 A | 2/2011 |
| JP | 2013-003478 A | 6/2011 |

OTHER PUBLICATIONS

Notice of Reasons for Refusal dated Jun. 11, 2019, for corresponding Japanese Patent Application No. 2016-115145. Submitted with a machine translation.

* cited by examiner

*Primary Examiner* — Yara B Green
(74) *Attorney, Agent, or Firm* — Muir Patent Law, PLLC

(57) ABSTRACT

In an X-ray imaging apparatus, an X-ray irradiation unit, an X-ray detection unit, a control unit configured to control irradiation of an X-ray, an X-ray image processing unit configured to operate independently of the control unit, and a storage battery for the X-ray image processing unit and the control unit are provided. The X-ray image processing unit is configured to acquire information on a remaining amount of the storage battery from the control unit and perform processing of reducing power consumption of the X-ray image processing unit when the remaining amount of the storage battery is equal to or less than a predetermined threshold value.

19 Claims, 6 Drawing Sheets

X-RAY IMAGING APPARATUS

CROSS-REFERENCE TO RELATED APPLICATIONS

The related application number JP2016-115145, entitled "X-ray imaging apparatus", filed on Jun. 9, 2016, and invented by Keita Gotoh, upon which this patent application is based is hereby incorporated by reference.

BACKGROUND OF THE INVENTION

Field of the Invention

The present invention relates to an X-ray imaging apparatus, and more particularly to an X-ray imaging apparatus equipped with a storage battery.

Description of the Background Art

Conventionally, an X-ray imaging apparatus equipped with a storage battery is known. Such an X-ray imaging apparatus is disclosed in, for example, Japanese Unexamined Patent Application Publication No. 2010-94327.

In Japanese Unexamined Patent Application Publication No. 2010-94327, an X-ray imaging apparatus is disclosed. The X-ray imaging apparatus is provided with an X-ray irradiation unit, an X-ray detection unit, a control unit configured to control irradiation of the X-ray from the X-ray irradiation unit, an X-ray image processing unit configured to be operable independently of the control unit and generate an X-ray image based on the X-ray detected by the X-ray detection unit, and a storage battery configured to supply power to the X-ray image processing unit and the control unit.

Note that, in a conventional X-ray imaging apparatus as disclosed in Japanese Unexamined Patent Application Publication No. 2010-94327, the X-ray image processing unit is configured to be operable independently of the control unit, and as long as power is continuously supplied from the storage battery, the X-ray image processing unit continuously operates. However, in a conventional X-ray imaging apparatus as disclosed in Japanese Unexamined Patent Application Publication No. 2010-94327, when the remaining amount of the storage battery decreases, over-discharge occurs to cause a forced shut-down. When over-discharge occurs, a load is imposed on the OS (Operating System) and files operating on the X-ray image processing unit, which is not preferable.

The present invention has been made to solve the aforementioned problems, and one object of the present invention is to provide an X-ray imaging apparatus capable of suppressing a forced shut-down from being performed on an X-ray image processing unit.

SUMMARY OF THE INVENTION

In order to attain the aforementioned object, an X-ray imaging apparatus according to one aspect of the present invention includes:

an X-ray irradiation unit configured to irradiate an X-ray to a subject;

an X-ray detection unit configured to detect the X-ray irradiated from the X-ray irradiation unit and has passed through the subject;

a control unit configured to control irradiation of the X-ray from the X-ray irradiation unit;

an X-ray image processing unit configured to be operable independently of the control unit and generate an X-ray image based on the X-ray detected by the X-ray detection unit; and a storage battery configured to supply power to the X-ray image processing unit and the control unit, wherein the X-ray image processing unit is configured to acquire information on a remaining amount of the storage battery from the control unit and perform processing of reducing power consumption of the X-ray image processing unit when an acquired remaining amount of the storage battery is equal to or less than a predetermined threshold value.

In the X-ray imaging apparatus according to one aspect of the present invention, as described above, the X-ray image processing unit is configured to acquire information on the remaining amount of the storage battery from the control unit and perform processing of reducing power consumption of the X-ray image processing unit when the acquired remaining amount of the storage battery is equal to or less than the predetermined threshold value. As a result, the power consumption of the X-ray image processing unit is reduced on the basis that the acquired remaining amount of the storage battery becomes equal to or less than the predetermined threshold value. Therefore, over-discharge can be suppressed. This in turn can suppress a forced shut-down from being performed on the X-ray image processing unit.

In the X-ray imaging apparatus according to the aforementioned one aspect of the present invention, the X-ray image processing unit is preferably configured to suspend processing of generating the X-ray image and save image data, and then perform the processing of reducing the power consumption of the X-ray image processing unit when the remaining amount of the storage battery received from the control unit is equal to or less than the predetermined threshold value. With this configuration, the processing of generating an X-ray image is suspended and image data is saved, so that the image data can be prevented from being lost.

In the X-ray imaging apparatus according to the aforementioned one aspect of the present invention, the X-ray imaging apparatus preferably further includes a notification unit configured to notify that the remaining amount of the storage battery has decreased when the remaining amount of the storage battery received from the control unit by the X-ray image processing unit has become equal to or less than the predetermined threshold value. With this configuration, the notification allows the user to immediately recognize that the remaining amount of the storage battery has become low, which makes it possible for the user to immediately take countermeasures, such as, e.g., charging.

In this case, the X-ray image processing unit is preferably configured to perform the processing of reducing the power consumption of the X-ray image processing unit after a predetermined first period has elapsed after performing a notification by the notification unit. By configuring as described above, after the first period from the notification, the X-ray image processing unit performs the processing of reducing the power consumption. Therefore, the notification can give the user a grace period (first period) for performing predetermined processing, such as, e.g., transferring of an image.

In the X-ray imaging apparatus according to the aforementioned one aspect of the present invention, the X-ray image processing unit is preferably configured to, when communication with the control unit becomes unavailable, acquire a predetermined second period based on the remaining amount of the storage battery acquired from the control unit immediately before communication with the control unit becomes unavailable, and perform the processing of reducing the power consumption of the X-ray image processing unit after the predetermined second period has elapsed from a point of time when the communication with the control unit becomes unavailable. Note that, since the X-ray image processing unit acquires information on the remaining amount of the storage battery from the control unit, when communication with the control unit is unavailable, it becomes obviously unavailable to acquire the remaining amount of the storage battery. So, by configuring as described above, even in cases where the X-ray imaging apparatus becomes unable to communicate with the control unit and therefore cannot get the remaining amount of the storage battery, it is possible to acquire a predetermined second period and execute processing of reducing the power consumption of the X-ray image processing unit. This enables suppressing of occurrence of over-discharge. This in turn can more effectively suppress a forced shut-down from being performed on the X-ray image processing unit.

In the X-ray imaging apparatus according to the aforementioned one aspect of the present invention, the X-ray image processing unit is preferably configured to, when the X-ray image processing unit cannot communicate with the control unit at the time of startup processing, suspend the startup processing of the X-ray image processing unit without acquiring information on the remaining amount of the storage battery from the control unit. By configuring as described above, when the remaining amount of the storage battery cannot be acquired, the startup processing of the X-ray image processing unit is suspended. Therefore, it is possible to prevent the power of the X-ray image processing unit from being consumed continuously without acquiring (knowing) the remaining amount of the storage battery. As a result, occurrence of over-discharge can be assuredly suppressed.

In the X-ray imaging apparatus according to the aforementioned one aspect of the present invention, the X-ray image processing unit is preferably configured to, when the remaining amount of the storage battery is greater than the predetermined threshold value and no operation by a user has been performed for a predetermined third period, preform the processing of reducing the power consumption of the X-ray image processing unit. By configuring as described above, it is possible to prevent unnecessary power consumption while the X-ray imaging apparatus is left unattended.

In the X-ray imaging apparatus according to the aforementioned one aspect of the present invention, the X-ray imaging apparatus preferably further includes a power supply unit connected to an external power source and configured to supply power to the control unit and the X-ray image processing unit, wherein the X-ray image processing unit is configured to, when power is being supplied from the external power source via the power supply unit, maintain a state of consuming normal power without performing the processing of reducing the power consumption of the X-ray image processing unit. By configuring as described above, when the X-ray imaging apparatus is connected to the external power source, power can be stably supplied, so it is possible to prevent execution of the processing of reducing the power consumption of the X-ray image processing unit.

In the X-ray imaging apparatus according to the aforementioned one aspect of the present invention, the processing of reducing the power consumption of the X-ray image processing unit preferably includes at least one of shut-down processing of making the X-ray image processing unit in a turned-off state and sleep processing of making the X-ray image processing unit in a stand-by state. By configuring as described above, by the shut-down processing, the X-ray image processing unit can be brought into zero power consumption. Further, by the sleep processing, it is possible to make the X-ray image processing unit in a stand-by state capable of immediately returning to the use state of the device. Note that the above-described shut-down means to turn off the power supply after terminating the OS and software operating on the OS. On the other hand, the above-describe forced shutdown means to turn off the power suddenly without terminating the OS and software running on the OS.

According to the present invention, as described above, it is possible to provide an X-ray imaging apparatus capable of suppressing forced shut-down to the X-ray image processing unit.

DESCRIPTION OF PREFERRED EMBODIMENTS

Hereinafter, embodiments of the present invention will be described with reference to the drawings.
(Configuration of Mobile X-ray Imaging Apparatus)

A configuration of a mobile X-ray imaging apparatus 100 according to an embodiment of the present invention will be described with reference to FIG. 1 and FIG. 2. Note that the mobile X-ray imaging apparatus 100 is an example of the "X-ray imaging apparatus" as recited in claims.

Figure 1:
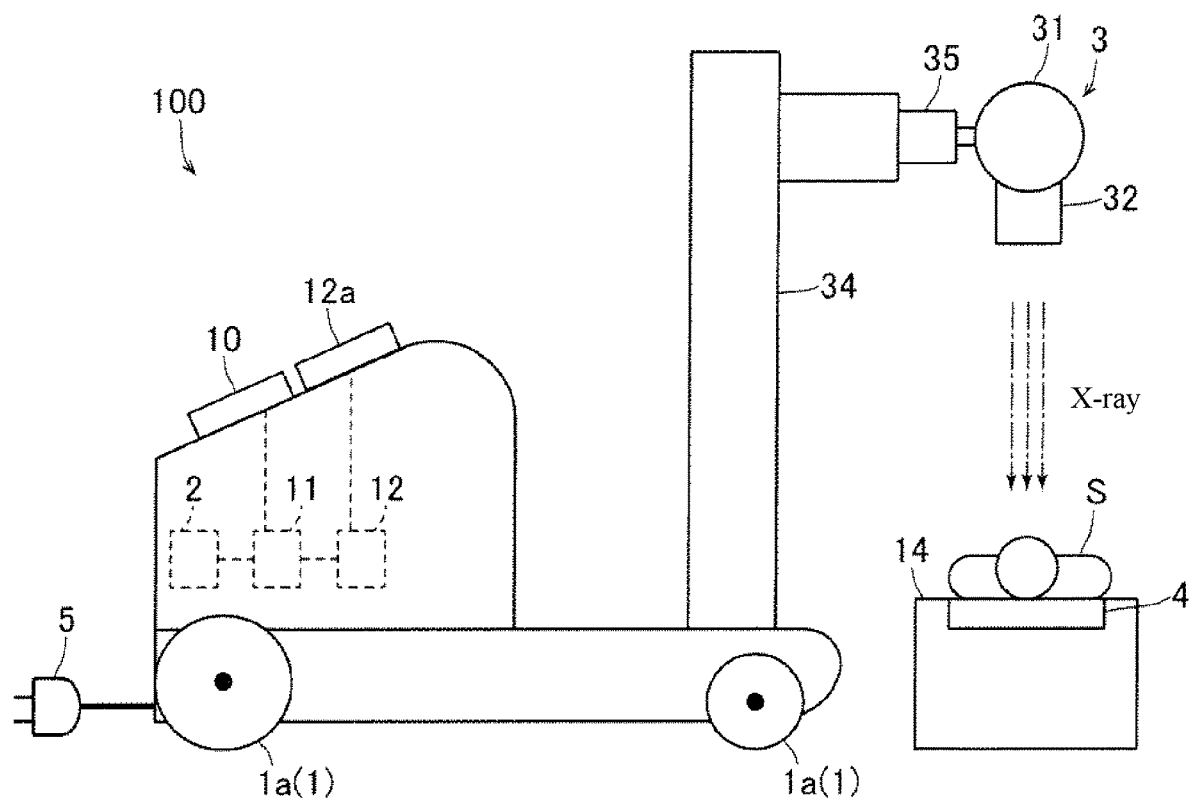
FIG. 1 is an external view showing an overall configuration of a mobile X-ray imaging apparatus according to an embodiment of the present invention.

As shown in FIG. 1, the mobile X-ray imaging apparatus 100 is equipped with a traveling drive mechanism 1 having drive wheels 1a and a storage battery 2. The mobile X-ray imaging apparatus 100 is configured to be movable to, for example, a patient who cannot move by driving the drive wheels 1a under the control by the control unit 11. Further, the mobile X-ray imaging apparatus 100 is configured to receive power supply from the storage battery 2 and drive each unit.

Figure 2:
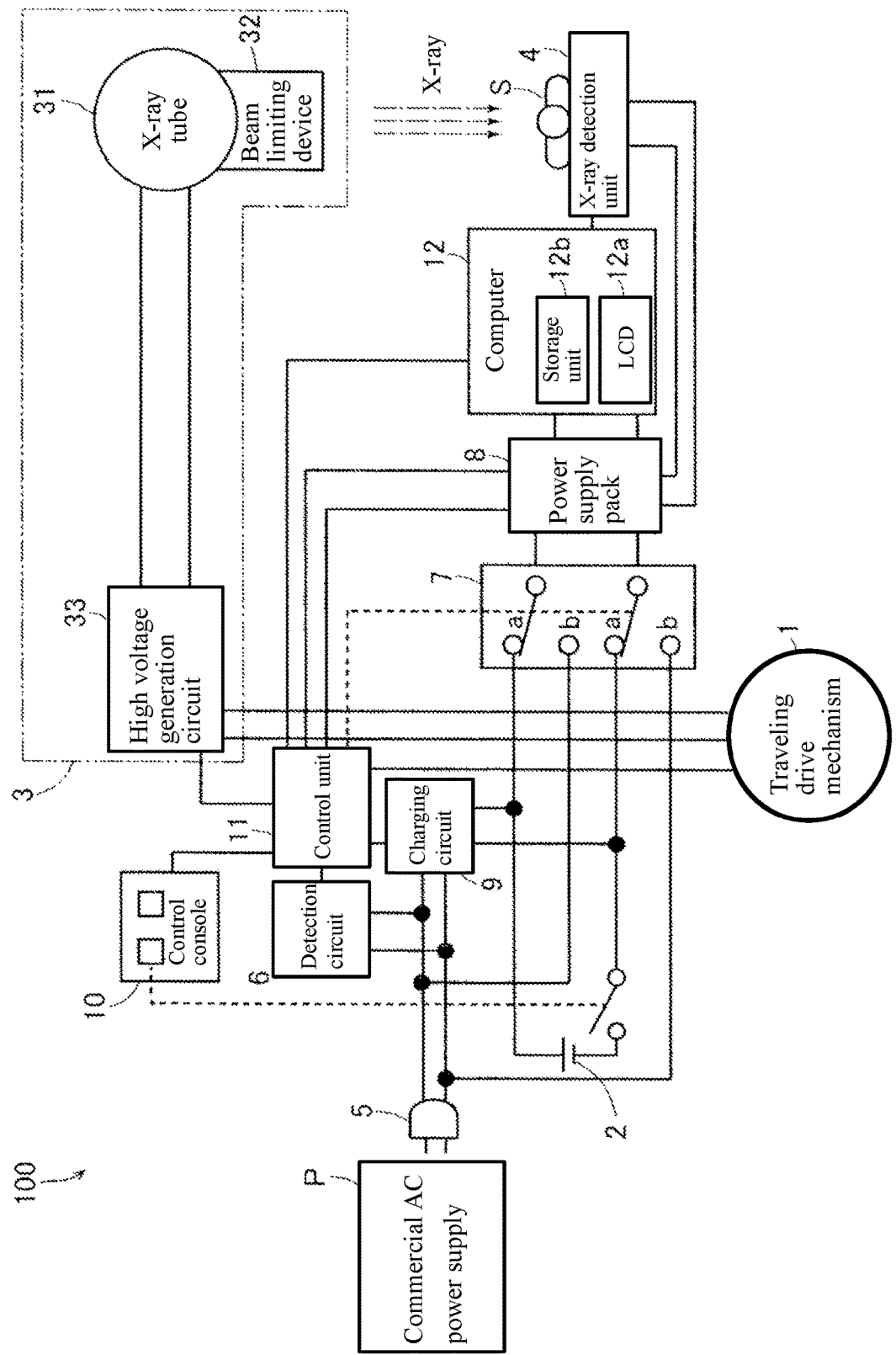
FIG. 2 is a block diagram showing an overall configuration of a mobile X-ray imaging apparatus according to an embodiment of the present invention.

As shown in FIG. 2, the mobile X-ray imaging apparatus 100 is further provided with an X-ray irradiation unit 3, an X-ray detection unit 4, a power supply plug 5, a detection circuit 6, a relay unit 7, a power supply pack 8, a charging circuit 9, a control console 10, a control unit 11, and a computer 12. It should be noted that the storage battery 2 is configured to individually supply power to the computer 12 and the control unit 11. Also note that the power supply plug 5 is an example of the "power supply unit" recited in claims. Also note that the computer 12 is an example of the "X-ray image processing unit" recited in claims.

The X-ray irradiation unit 3 includes an X-ray tube 31, a beam limiting device 32, a high voltage generation circuit 33, a support column 34 (see FIG. 1), and an arm 35 (see FIG. 1).

The X-ray tube 31 is arranged so as to face the X-ray detection unit 4 across the top board 14 (see FIG. 1) on which the subject S is to be placed. Further, the X-ray tube 31 is configured to irradiate an X-ray to the subject S. The beam limiting device 32 is attached to the tip of the X-ray tube 31, and is configured so as to limit the irradiation range of the X-ray by narrowing the X-ray. Further, the high voltage generation circuit 33 is configured to supply a high voltage to the X-ray tube 31. As shown in FIG. 1, the support column 34 is a columnar member extending in the vertical direction, and the arm 35 is attached near the upper end portion of the support column 34. Further, the support column 34 is configured to be freely rotatable and extendable in the vertical direction. The arm 35 extends in the horizontal direction, and the X-ray tube 31 and the beam limiting device 32 are attached to the tip of the arm 35. Further, the arm 35 is configured to be expandable and contractible in the horizontal direction.

As shown in FIG. 2, the X-ray detection unit 4 is configured to detect the X-ray irradiated from the X-ray tube 31 and passed through the subject S. The X-ray detection unit 4 is configured to capture an X-ray image based on the detected X-ray. Specifically, the X-ray detection unit 4 is configured to convert the detected X-ray into an electric signal. Further, the information of the X-ray converted into the electric signal is transmitted to the computer 12. The transmission at this time is performed by wired communication or wireless communication via a communication unit (not shown).

The power supply plug 5 is connected to the commercial AC power supply P and is configured to supply power to each part of the mobile X-ray imaging apparatus 100, such as, e.g., the control unit 11 and the computer 12. Note that the commercial AC power supply P is an example of the "external power source" recited in claims.

The detection circuit 6 is configured to transmit a detection signal concerning the connection of the power supply plug 5 with respect to the commercial AC power supply P and the connection release of the power supply plug 5 with respect to the commercial AC power supply P to the control unit 11 and the computer 12.

When the power supply plug 5 is connected to the commercial AC power supply P, the relay unit 7 is configured to switch the power supply source from the storage battery 2 to the commercial AC power supply P under the control of the control unit 11. Specifically, the relay unit 7 is configured to switch from the contact a to the contact b. On the other hand, when the connection release of the power supply plug 5 with respect to the commercial AC power supply P is performed, the relay unit 7 is configured to switch the power supply source from the commercial AC power supply P to the storage battery 2. Specifically, the relay unit 7 is configured to switch from the contact b to the contact a.

The power supply pack 8 is configured so that power is supplied from the storage battery 2 when the relay unit 7 is at the contact a. Further, the power supply pack 8 is configured so that power is supplied from the commercial AC power supply P when the relay unit 7 is at the contact b. The power supply pack 8 is configured to supply the power supplied from the storage battery 2 or the commercial AC power supply P to each part of the mobile X-ray imaging apparatus 100.

The charging circuit 9 is configured to charge the storage battery 2 with the commercial AC power supply P when the power supply plug 5 is connected to the commercial AC power supply P.

The control console 10 is provided with various switches for accepting various operations from a user. Specific examples of the switch include a power switch which makes it possible to supply electric power to each part (excluding the computer 12), such as, e.g., the X-ray irradiation unit 3 and the traveling drive mechanism 1, and an image capturing start switch.

The control unit 11 is configured to control irradiation of the X-ray from the X-ray irradiation unit 3. Further, the control unit 11 is configured to control the driving of the mobile X-ray imaging apparatus 100. Further, the control unit 11 is configured to acquire the information on the remaining amount of the storage battery 2 via the power supply pack 8 connected to the storage battery 2. Further, the control unit 11 is configured to transmit the information on the acquired remaining amount of the storage battery 2 to the computer 12.

The computer 12 is configured to generate an X-ray image based on the electric signal of the X-ray detected by the X-ray detection unit 4. Further, the computer 12 is configured to be operable independently of the control unit 11. In other words, the computer 12 and the control unit 11 are configured so as to be able to turn on and off the power supply separately.

The computer 12 is configured to acquire the information on the remaining amount of the storage battery 2 from the control unit 11, and perform processing of decreasing the power consumption of the computer 12 when the acquired remaining amount of the acquired storage battery 2 is equal to or less than the predetermined threshold value $\alpha$. Note that the computer 12 cannot acquire the information on the remaining amount of the storage battery 2 when the power of the control unit 11 is turned off or when communication with the control unit 11 cannot be performed for some reason, such as, e.g., communication abnormality.

The computer 12 includes a liquid crystal display (LCD) 12a. As shown in FIG. 1, the liquid crystal display 12a is arranged side by side with the control console 10. Further, the liquid crystal display 12a shown in FIG. 2 is configured to display a predetermined dialog notifying that the remaining amount of the storage battery 2 has become smaller when the remaining amount of the storage battery 2 received by the computer 12 from the control unit 11 has become equal to or less than a predetermined threshold value $\alpha$. Specifically, the liquid crystal display 12a is configured to display that shut-down occurs after a predetermined first period (for example, 10 minutes) has elapsed due to the small remaining amount of the storage battery 2 when the remaining amount of the storage battery received by the computer 12 from the control unit 11 has become equal to or less than the predetermined threshold value $\alpha$. Note that the liquid crystal display 12a is an example of the "notification unit" recited in claims. Also note that the threshold value $\alpha$ is an example of the "threshold value" recited in claims.

The computer 12 is configured to perform the notification by the liquid crystal display 12a and then shut down in order to perform the processing of decreasing the power consumption of the computer 12 after a predetermined first period has elapsed. Note that the computer 12 includes a storage unit 12b and is configured to, when shutting down, suspend the processing of generating an X-ray image, save the image data in the storage unit 12b, and then perform the processing of decreasing the power consumption of the computer 12. Note that the above-described suspending of the processing of generating the X-ray image means suspending of the predetermined study performed by irradiating the X-ray against the subject S.

The above-described series of processing (processing of performing the notification by the liquid crystal display 12a, processing of suspending the processing of generating an X-ray image after the first period has elapsed, processing of saving the image data in the storage unit 12b, shutting down for executing processing of reducing the power consumption of the computer 12 after the first period has elapsed) corresponds to the processing of reducing the power consumption of the computer 12.

When the computer 12 has become unavailable to communicate with the control unit 11, the computer 12 is configured to perform as follows. That is, the computer 12 acquires a predetermined second period based on the remaining amount of the storage battery 2 acquired from the control unit 11 immediately before the communication with the control unit 11 has become unavailable, and shuts down to reduce the power consumption of the computer 12 after the second period has elapsed from the point of time when the computer 12 has become unavailable to communicate with the control unit 11. The predetermined second period may be calculated from the remaining amount of the storage battery 2, or may be acquired from a predetermined table in which the remaining amount of the storage battery 2 and the remaining usable period for the remaining amount of the storage battery 2 are associated with each other. Further, the case in which the computer 12 has become unavailable to communicate with the control unit 11 is exemplified by, for example, a case in which the control unit 11 is simply turned off, and a case in which communication with the control unit 11 becomes unavailable due to some abnormality.

The computer 12 is provided with an operation unit (not shown) for accepting various operations from a user. For example, the computer 12 is provided with an operation unit, such as, e.g., a keyboard and a mouse. Besides this, the liquid crystal display 12a may be configured by a touch panel so that various operations from a user can be accepted.

When the computer 12 cannot communicate with the control unit 11 at the time of the startup operation of the computer 12, the computer 12 is configured to suspend the startup processing of the computer 12 without acquiring information on the remaining amount of the storage battery 2 from the control unit 11.

When the remaining amount of the storage battery 2 is larger than the predetermined threshold value α and the operation by the user is not performed for a predetermined third period, the computer 12 is configured to shut down to reduce the power consumption of the computer 12.

When electric power is supplied from the commercial AC power supply P via the power supply plug 5, the computer 12 is configured to maintain the state of consuming normal electric power without shutting down in order to reduce the power consumption of the computer 12. That is, the computer 12 does not shut-down if power is stably supplied from the commercial AC power supply P.
(Processing when Computer Communication is Available)

Figure 3:
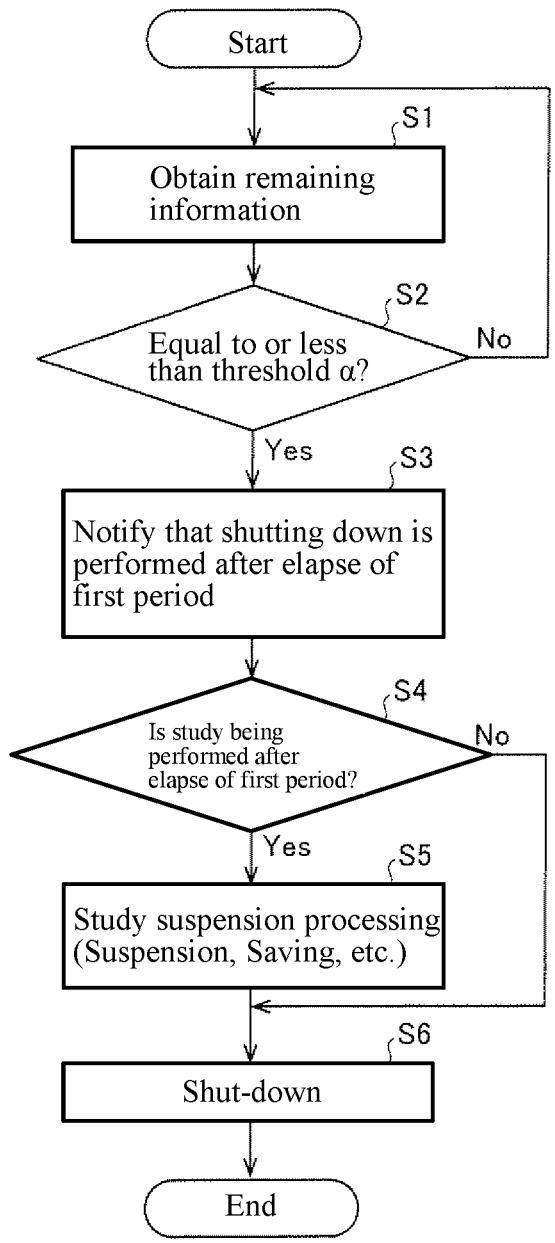
FIG. 3 is a flowchart for explaining shut-down processing of a computer when communication between the computer and a control unit is available according to an embodiment of the present invention.

Next, with reference to FIG. 3, the shut-down process flow when the computer 12 can communicate with the control unit 11 will be described. In the following description, the state in which the power supply plug 5 is not connected to the commercial AC power supply P will be described.

First, in Step S1, the information on the remaining amount of the storage battery 2 is acquired from the control unit 11. Next, in Step S2, it is determined whether or not the acquired remaining amount of the storage battery 2 is equal to or less than the threshold value α. When the acquired remaining amount (value) of the storage battery 2 is larger than the threshold value α, the process returns to Step S1 and the information on the remaining amount of the storage battery 2 is acquired again. On the other hand, when the acquired remaining amount (value) of the storage battery 2 is equal to or less than the threshold value α, the process proceeds to Step S3. In this way, the computer 12 constantly monitors the remaining amount of the storage battery 2 by repeatedly acquiring the information on the remaining amount of the storage battery 2 from the control unit 11.

In Step S2, when the acquired remaining amount of the storage battery 2 is equal to or less than the threshold value α, the process proceeds to Step S3. In Step S3, a predetermined dialog is displayed on the liquid crystal display 12a, and a notification to shut down after a predetermined first period (for example, 10 minutes) has elapsed is performed.

Next, in Step S4, after the predetermined first period has elapsed, it is determined whether or not a predetermined study by the mobile X-ray imaging apparatus 100 is being performed. When the study is being performed, suspension processing of the study (processing of suspending the study and processing of storing the image data) is performed. Thereafter, the process proceeds to Step S6. When the study is not been performed, the process proceeds to Step S6 without proceeding to Step S5.

Next, in Step S6, shut-down is performed in order to reduce the power consumption of the computer 12.
(Processing when Computer Communication is Unavailable)

Figure 4:
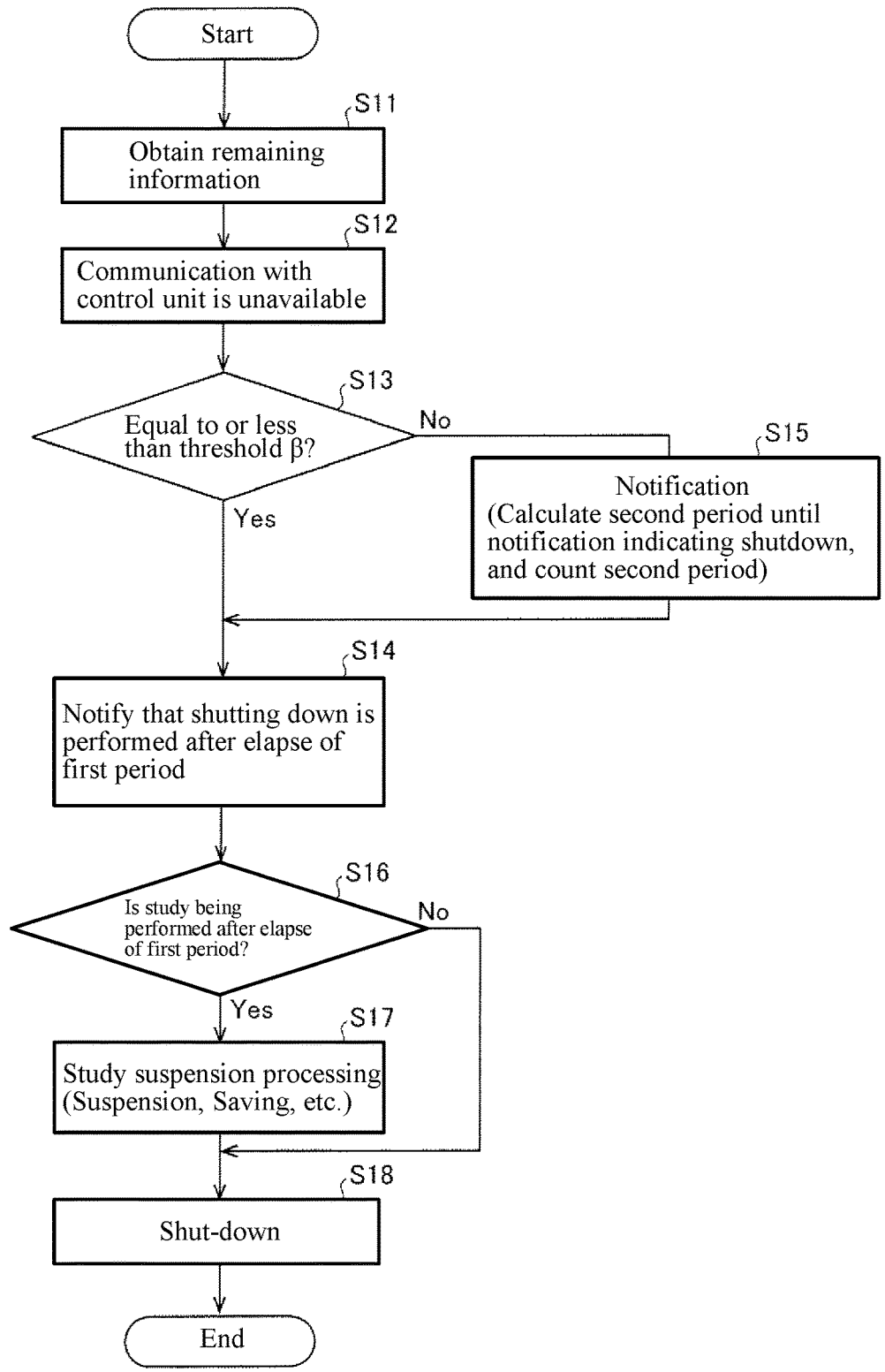
FIG. 4 is a flowchart for explaining shut-down processing of a computer when communication between the computer and a control unit is unavailable according to an embodiment of the present invention.

Next, with reference to FIG. 4, the shut-down process flow when the computer 12 cannot communicate with the control unit 11 will be described. In the following description, the state in which the power supply plug 5 is not connected to the commercial AC power supply P will be described.

First, in Step S11, the information on the remaining amount of the storage battery 2 is acquired from the control unit 11. Then, in Step S12, it is detected that the state in which communication with the control unit 11 is available has been changed to the state in which communication with the control unit 11 is not available. When the remaining amount of the storage battery 2 is equal to or less than the threshold value α at the time point up to this Step S12, the processes of the above-described Steps S3 to S6 are performed without performing Steps S13 to S18 described below.

Next, in Step S13, it is determined whether or not the remaining amount of the storage battery 2 acquired immediately before the communication with the control unit 11 has become unavailable is equal to or less than the threshold value β. The threshold value β is a value equal to or larger than the threshold value α.

Then, in Step S13, when the remaining amount of the storage battery 2 acquired immediately before communication with the control unit 11 has become unavailable is equal to or less than the threshold value β, the process proceeds to Step S14. The subsequent Steps S14, and S16 to S18 are the same as the above-described Steps S3 to S6, and therefore the description thereof will be omitted.

In Step S13, when the remaining amount of the storage battery 2 acquired immediately before communication with the control unit 11 has become unavailable is larger than the threshold value β, the process proceeds to Step S15. Next, in Step S15, the second time (a period of waiting until a notification) (for example, 30 minutes) until "a predetermined dialog is displayed on the liquid crystal display 12a and the notification (Step S14) indicating that the shutting down will be performed after a predetermined first period (for example, 10 minutes) has elapsed" is performed is acquired (calculated) from the remaining amount of the storage battery 2 acquired immediately before the communication with the control unit 11 has become unavailable to count the second period. After completion of counting the second period, the process proceeds to Step S14.

(Processing when Starting up the Computer)

Figure 5:
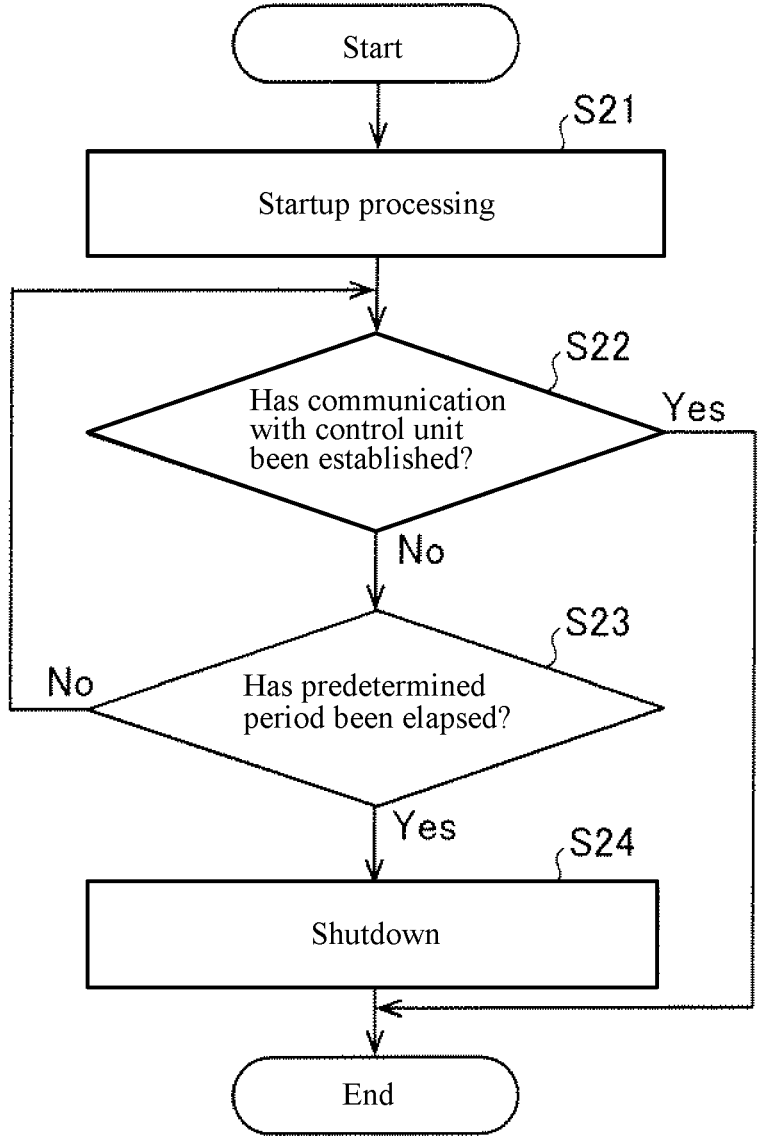
FIG. 5 is a flowchart for explaining processing at the time of computer startup according to an embodiment of the present invention.

Next, with reference to FIG. 5, a process flow at the time of starting up the computer 12 will be described. In the following description, the state in which the power supply plug 5 is not connected to the commercial AC power supply P will be described.

First, in Step S21, startup processing of the computer 12 is initiated. Next, in Step S22, an operation of establishing the communication with the control unit 11 is performed, and it is determined whether or not communication has been established. When communication with the control unit 11 is established, startup processing is completed. To the contrary, when communication with the control unit 11 is not established, the process proceeds to Step S23. Next, in Step S23, it is determined whether or not a predetermined time has elapsed since the startup processing of the computer 12 was initiated. If the predetermined time has not elapsed since the startup processing of the computer 12 was started, the process returns to Step S22. If the predetermined time has elapsed since the startup processing of the computer 12 was started, the process proceeds to Step S24. In other words, when communication with the control unit 11 cannot be established even after the predetermined time has elapsed, the communication establishment is given up and the process proceeds to Step S24.

Next, in Step S24, shutting down of the computer 12 is performed. The reason that the shutting down is performed is that the computer 12 cannot establish communication with the control unit 11 and cannot acquire the remaining amount of the storage battery 2. That is, it is not preferable to continuously use the computer 12 in a state in which the computer 12 cannot acquire the remaining amount of the storage battery 2.

(Processing when No Operation of the Computer has been Continued)

Figure 6:
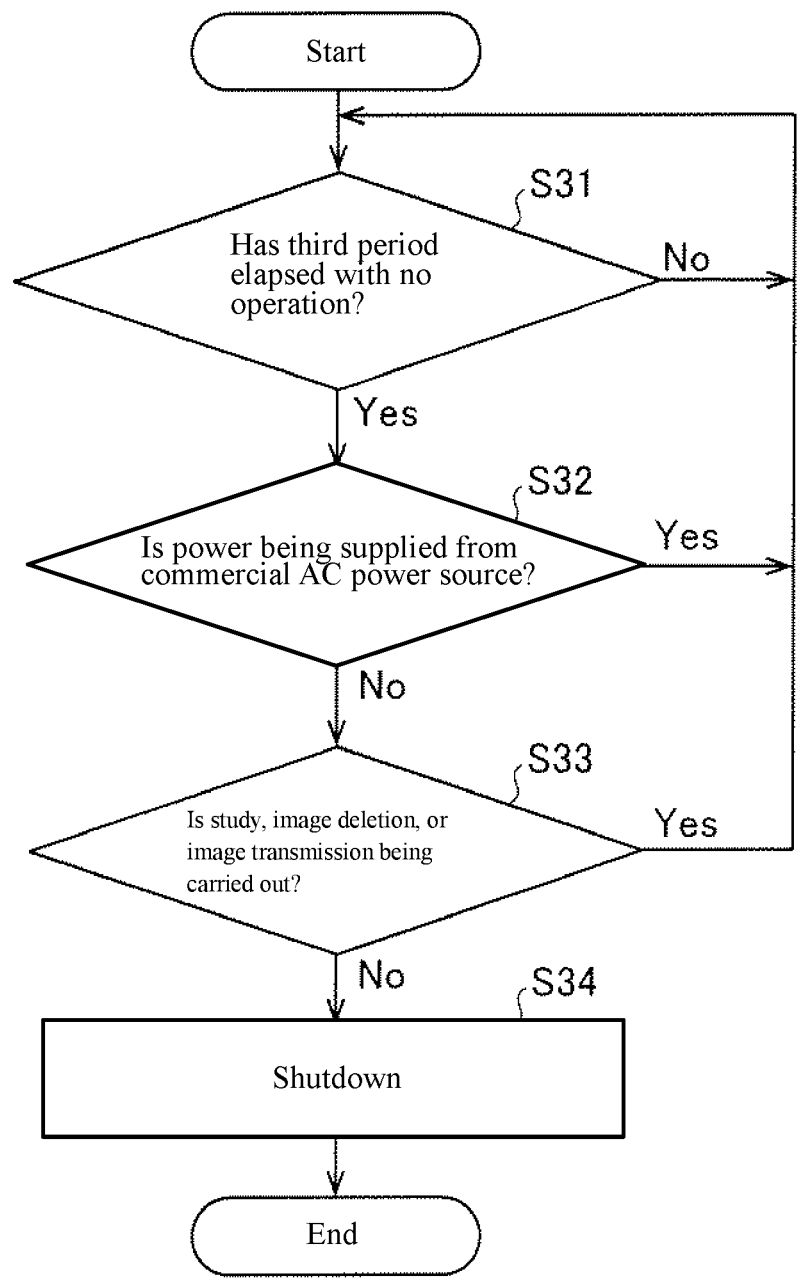
FIG. 6 is a flowchart for explaining the processing when no operation of a computer has been continued according to an embodiment of the present invention.

Next, with reference to FIG. 6, a process flow is shown when operations of the computer 12 have been absent over a continuous period (the state in which no operations of the computer 12 by any user have been continuous over a predetermined time period).

In Step S31, it is determined whether or not the third period (e.g., 30 minutes) has elapsed in a state in which the computer 12 has not been used by any operator at any time during the third period (e.g., a lack of use over a predetermined time period). If the third period without operator use has not elapsed, the process repeats Step S31. If the third period has elapsed, the process proceeds to Step S32.

Next, in Step S32, it is determined whether or not electric power is being supplied from the commercial AC power supply P to the computer 12 via the power supply plug 5. When electric power is being supplied from the commercial AC power supply P via the power supply plug 5, the process returns to Step S31. When electric power is not being supplied from the commercial AC power supply P via the power supply plug 5, the process proceeds to Step S33.

Next, in Step S33, it is determined whether or not at least one of a study (surgery), an image deletion, and an image transmission is being performed. That the study (surgery) is being performed means that, for example, dedicated software for a study (surgery) is started on the computer 12 and a predetermined button for starting the study (surgery) is pushed, so that the study (surgery) is taking place. If at least one of the study (surgery), the image deletion, and the image transmission is being performed, the process returns to Step S31. If none of the inspection (surgery), the image deletion, and the image transmission is being performed, the process proceeds to Step S34, and shutting down of the computer 12 is performed.

Effects of this Embodiment

In this embodiment, the following effects can be acquired.

In this embodiment, as described above, the computer 12 is configured to acquire the information on the remaining amount of the storage battery 2 from the control unit 11, and perform processing of decreasing the power consumption of the computer 12 when the acquired amount of the acquired storage battery 2 is equal to or less than the predetermined threshold value α. As a result, the power consumption of the computer 12 is reduced on the basis that the acquired remaining amount of the storage battery 2 becomes equal to or less than the predetermined threshold value. Therefore, over-discharge can be suppressed. This in turn can suppress a forced shut-down from being performed on the computer 12.

Further, in this embodiment, as described above, the computer 12 is configured to suspend processing of generating the X-ray image and save image data, and then perform processing of reducing power consumption of the computer 12 when the remaining amount of the storage battery 2 received from the control unit 11 is equal to or less than the predetermined threshold value. With this configuration, the processing of generating the X-ray image is suspended and image data is saved, so that the image data can be prevented from being lost.

Further, in this embodiment, as described above, the liquid crystal display 12a configured to notify that the remaining amount of the storage battery 2 has become smaller when the remaining amount of the storage battery 2 received by the computer 12 from the control unit 11 has become equal to or less than the predetermined threshold value. With this configuration, the notification allows the user to immediately recognize that the remaining amount of the storage battery has become low, which makes it possible for the user to immediately take countermeasures, such as, e.g., charging.

Further, in this embodiment, as described above, the computer 12 is configured to perform the notification by the liquid crystal display 12a and then shut down in order to perform the processing of decreasing the power consumption of the computer 12 after a predetermined first period has elapsed. With this, after the first period from the notification, the computer 12 performs the processing of reducing the power consumption. Therefore, the notification can give the user a grace period (first period) for performing predetermined processing, such as, e.g., an image transfer.

Further, in this embodiment, as described above, when communication with the control unit 11 has become unavailable, the computer 12 is configured to perform as follows. That is, the computer 12 acquires a predetermined second period based on the remaining amount of the storage battery 2 acquired from the control unit 11 immediately before the communication with the control unit 11 has become unavailable, and shuts down to reduce the power consumption of the computer 12 after the second period has elapsed from the point of time when communication with the control unit 11 has become unavailable. Note that, since the computer 12 acquires the information on the remaining amount of the storage battery 2 from the control unit 11, when the computer 12 cannot communicate with the control unit 11, it becomes obviously unavailable to acquire the remaining amount of the storage battery. So, by configuring as described above, even in cases where the computer 12 cannot communicate with the control unit 11 and therefore the remaining amount of the storage battery 2 cannot be acquired, it is possible to perform processing of acquiring the predetermined second period and reducing the power consumption of the computer 12. Thus, over-discharge can be suppressed. As a result, this in turn can more suppress a forced shut-down from being performed on the computer 12.

Further, in this embodiment, as described above, when the computer 12 cannot communicate with the control unit 11 at the time of the startup operation of the computer 12, the computer 12 is configured to suspend the startup processing of the computer 12 without acquiring information on the remaining amount of the storage battery 2 from the control unit 11. With this, when the remaining amount of the storage battery 2 cannot be acquired, the startup processing of the computer 12 is suspended. Therefore, it is possible to prevent the power of the computer 12 from being consumed continuously without acquiring (knowing) the remaining amount of the storage battery 2. As a result, occurrence of over-discharge can be assuredly suppressed.

Further, in this embodiment, as described above, when the remaining amount of the storage battery 2 is larger than the predetermined threshold value and the operation by a user is not performed for a predetermined third period, the computer 12 is configured to reduce the power consumption of the computer 12. With this, it is possible to prevent wasteful power consumption while the mobile X-ray imaging apparatus 100 is left unattended.

Further, in this embodiment, as described above, when a power supply plug 5 connected to the commercial AC power supply P to supply electric power to the control unit 11 and the computer 12 is provided and when power is being supplied from the commercial AC power supply P via the power supply plug 5 to the computer 12, it is configured such that the processing of reducing the power consumption of the computer 12 is not performed and the state of consuming the normal power is maintained. With this, when connected to the commercial AC power supply P, power can be stably supplied, so it is possible to prevent processing of reducing the power consumption of the computer 12 from being performed.

Modified Embodiment

It should be understood that the embodiments disclosed here are examples in all respects and are not restrictive. The scope of the present invention is shown by the scope of the claims rather than the descriptions of the embodiments described above, and includes all changes (modifications) within the meaning of equivalent and the scope of claims.

For example, in the aforementioned embodiment, as the processing of reducing the power consumption of computer, an example in which when the remaining amount of the storage battery acquired by the computer is equal to or less than the predetermined threshold value, a notification that shutting down is performed after the first period has elapsed and the shutting down is performed after the first period has elapsed is exemplified, but the present invention is not limited. In the present invention, when the remaining amount of the storage battery acquired by the computer is equal to or less than the predetermined threshold value, shutting down may be performed without issuing the notification indicating the shutting down. In this case, shutting down is performed without waiting for the elapse of the first period.

Further, in the aforementioned embodiment, an example using a liquid crystal display is shown as an example of the notification unit of the present invention, but the present invention is not limited to this. In the present invention, as the notification unit of the present invention, a configuration in which notification is made by voice and/or blinking light may be used.

Further, in the aforementioned embodiment, an example in which the X-ray imaging apparatus of the present invention is configured by a mobile X-ray imaging apparatus is shown, but the present invention is not limited thereto. In the present invention, the X-ray imaging apparatus of the present invention may be configured by a fixed type X-ray imaging apparatus that does not move.

Further, in the aforementioned embodiment, as the processing of reducing the power consumption of the computer, an example in which shutting down is performed is shown, but the present invention is not limited to this. In the present invention, sleep may be performed instead of shutting down as the processing of reducing the power consumption of the computer. Note that sleep includes a standby mode that suppresses the power supply of the computer and puts the computer into a standby mode that allows the computer to immediately return to the normal state and a pause mode that saves the work state and turns off a part of the power supply of the computer.

Further, in the aforementioned embodiment, for the sake of convenience of explanation, the description has been made using the flow driven type flowchart in which the control processing of the computer is sequentially performed along the control processing flow, but the present invention is not limited thereto. In the present invention, the control processing of the computer may be performed by event driven type processing that performs processing in units of events. In this case, it may be performed in a completely event driven manner, or a combination of event driving and flow driving may be performed.

The invention claimed is:

1. An X-ray imaging apparatus comprising:
   an X-ray irradiation unit configured to irradiate an X-ray to a subject;
   an X-ray detection unit configured to detect the X-ray irradiated from the X-ray irradiation unit and has passed through the subject;
   a control unit configured to control irradiation of the X-ray from the X-ray irradiation unit;
   an X-ray image processing unit configured to be operable independently of the control unit and generate an X-ray image based on the X-ray detected by the X-ray detection unit; and
   a storage battery configured to supply power to the X-ray image processing unit and the control unit, wherein the control unit is configured to acquire information on a remaining amount of the storage battery;

wherein the X-ray image processing unit is configured to acquire information on the remaining amount of the storage battery from the control unit and perform processing of reducing power consumption of the X-ray image processing unit when an acquired remaining amount of the storage battery is equal to or less than a predetermined threshold value;

wherein the X-ray image processing unit is configured to, when communication with the control unit becomes unavailable, acquire a non-communication period based on the remaining amount of the storage battery acquired from the control unit immediately before the communication with the control unit becomes unavailable, and perform the processing of reducing the power consumption of the X-ray image processing unit after the non-communication period has elapsed from a point of time when the communication with the control unit becomes unavailable.

2. The X-ray imaging apparatus as recited in claim 1, wherein the X-ray image processing unit is configured to suspend processing of generating the X-ray image and save image data, and then perform the processing of reducing the power consumption of the X-ray image processing unit when the remaining amount of the storage battery received from the control unit is equal to or less than the predetermined threshold value.

3. The X-ray imaging apparatus as recited in claim 1, further comprising:
a notification unit configured to notify that the remaining amount of the storage battery has decreased when the remaining amount of the storage battery received from the control unit by the X-ray image processing unit has become equal to or less than the predetermined threshold value.

4. The X-ray imaging apparatus as recited in claim 1, wherein the X-ray image processing unit is configured to, when the X-ray image processing unit cannot communicate with the control unit at the time of startup processing, suspend the startup processing of the X-ray image processing unit without acquiring information on the remaining amount of the storage battery from the control unit.

5. The X-ray imaging apparatus as recited in claim 1, wherein the X-ray image processing unit is configured to, when the remaining amount of the storage battery is greater than the predetermined threshold value and no operation by a user has been performed for a non-operation period, perform the processing of reducing the power consumption of the X-ray image processing unit.

6. The X-ray imaging apparatus as recited in claim 1, further comprising:
a power supply unit connected to an external power source and configured to supply power to the control unit and the X-ray image processing unit,
wherein the X-ray image processing unit is configured to, when power is being supplied from the external power source via the power supply unit, maintain a state of consuming normal power without performing the processing of reducing the power consumption of the X-ray image processing unit.

7. The X-ray imaging apparatus as recited in claim 1, wherein the processing of reducing the power consumption of the X-ray image processing unit includes at least one of shut-down processing of making the X-ray image processing unit in a turned-off state and sleep processing of making the X-ray image processing unit in a stand-by state.

8. The X-ray imaging apparatus as recited in claim 1, wherein the X-ray image processing unit is a computer, and wherein the reducing the power consumption is a standby mode that suppresses a power supply of the computer and puts the computer into a standby mode that allows the computer to immediately return to a normal state.

9. The X-ray imaging apparatus as recited in claim 1, wherein the X-ray image processing unit is a computer, and wherein the reducing the power consumption is a pause mode that saves the work state and turns off a part of a power supply of the computer.

10. The X-ray imaging apparatus as recited in claim 1, wherein the non-communication period is calculated from the remaining amount of the storage battery.

11. The X-ray imaging apparatus as recited in claim 1, wherein the non-communication period is acquired from a predetermined table in which the remaining amount of the storage battery and the remaining usable period for the remaining amount of the storage battery are associated with each other.

12. The X-ray imaging apparatus as recited in claim 1, wherein communication with the control unit becomes unavailable is due to the control unit being turned off.

13. The X-ray imaging apparatus as recited in claim 1, wherein the communication with the control unit becomes unavailable due to an abnormality.

14. The X-ray imaging apparatus as recited in claim 1, further comprising wheels so as to be movable to a patient who cannot be moved.

15. An X-ray imaging apparatus comprising:
an X-ray irradiation unit configured to irradiate an X-ray to a subject;
an X-ray detection unit configured to detect the X-ray irradiated from the X-ray irradiation unit and has passed through the subject;
a control unit configured to control irradiation of the X-ray from the X-ray irradiation unit;
an X-ray image processing unit configured to be operable independently of the control unit and generate an X-ray image based on the X-ray detected by the X-ray detection unit; and
a storage battery configured to supply power to the X-ray image processing unit and the control unit;
a notification unit configured to notify that the remaining amount of the storage battery has decreased when the remaining amount of the storage batter received from the control unit by the X-ray image processing unit has become equal to or less than the predetermined threshold value;
wherein the control unit is configured to acquire information on a remaining amount of the storage battery;
wherein the X-ray image processing unit is configured to acquire information on the remaining amount of the storage battery from the control unit and perform processing of reducing power consumption of the X-ray image processing unit when an acquired remaining amount of the storage battery is equal to or less than a predetermined threshold value
and wherein the X-ray image processing unit is configured to perform the processing of reducing the power consumption of the X-ray image processing unit after a post-notification period has elapsed after performing a notification by the notification unit.

16. The X-ray imaging apparatus as recited in claim 15, wherein the notification unit is an LCD screen.

17. The X-ray imaging apparatus as recited in claim 16, wherein the notification is a remaining amount of the storage battery.

18. The X-ray imaging apparatus as recited in claim 15, wherein the notification is a time period remaining before the reducing of power consumption.

19. The X-ray imaging apparatus as recited in claim 15, wherein the notification allows the user to recognize that the remaining amount of the storage battery has become low, which makes it possible for the user to take countermeasures.

* * * * *